United States Patent
Tanihata

[11] Patent Number: 5,979,250
[45] Date of Patent: Nov. 9, 1999

[54] AUTOMATIC SAMPLER

[75] Inventor: Hiroshi Tanihata, Kyoto, Japan

[73] Assignee: Shimadzu Corporation, Kyoto, Japan

[21] Appl. No.: 08/982,456

[22] Filed: Dec. 2, 1997

[30] Foreign Application Priority Data

Dec. 13, 1996 [JP] Japan ................................ 8-333203

[51] Int. Cl.⁶ ................................................ G01N 1/00
[52] U.S. Cl. ................................ 73/863.01; 73/864.31; 73/864.91
[58] Field of Search ........................ 73/863, 863.01, 73/863.56, 864.91, 964.31; 422/63, 64; 414/24, 225

[56] References Cited

U.S. PATENT DOCUMENTS

5,215,923  6/1993  Kinoshita et al. ................. 414/225
5,305,650  4/1994  Koike et al. ...................... 73/864.21

*Primary Examiner*—Hezron Williams
*Assistant Examiner*—Thuy Vinh Tran
*Attorney, Agent, or Firm*—Kanesaka & Takeuchi

[57] ABSTRACT

An automatic sampler of the invention holds a sample properly. The automatic sampler is formed of a sample holding section, and a moving mechanism attached to the sample holding section. The moving mechanism moves the sample holding section in plural directions to transfer the sample held by the sample holding section. The sample holding section has a holding mechanism, and at least three fingers projecting downwardly from the holding mechanism. When the holding mechanism is actuated, a space defined among the fingers is regulated to hold the sample by the fingers. Each finger has an elongated circular member with an elastic portion at least at an outer surface thereof, and is freely rotatably attached to the holding mechanism. Thus, when the sample is held by the fingers, the fingers are properly located on the sample to surely hold the sample.

8 Claims, 8 Drawing Sheets

CENTRAL POSITION
AMONG FOUR FINGERS 11

AUTOMATIC SAMPLER

BACKGROUND OF THE INVENTION AND RELATED ART STATEMENT

The present invention relates to an automatic sampler for providing samples to an analyzer, such as a gas chromatograph and a liquid chromatograph.

Figure 4:
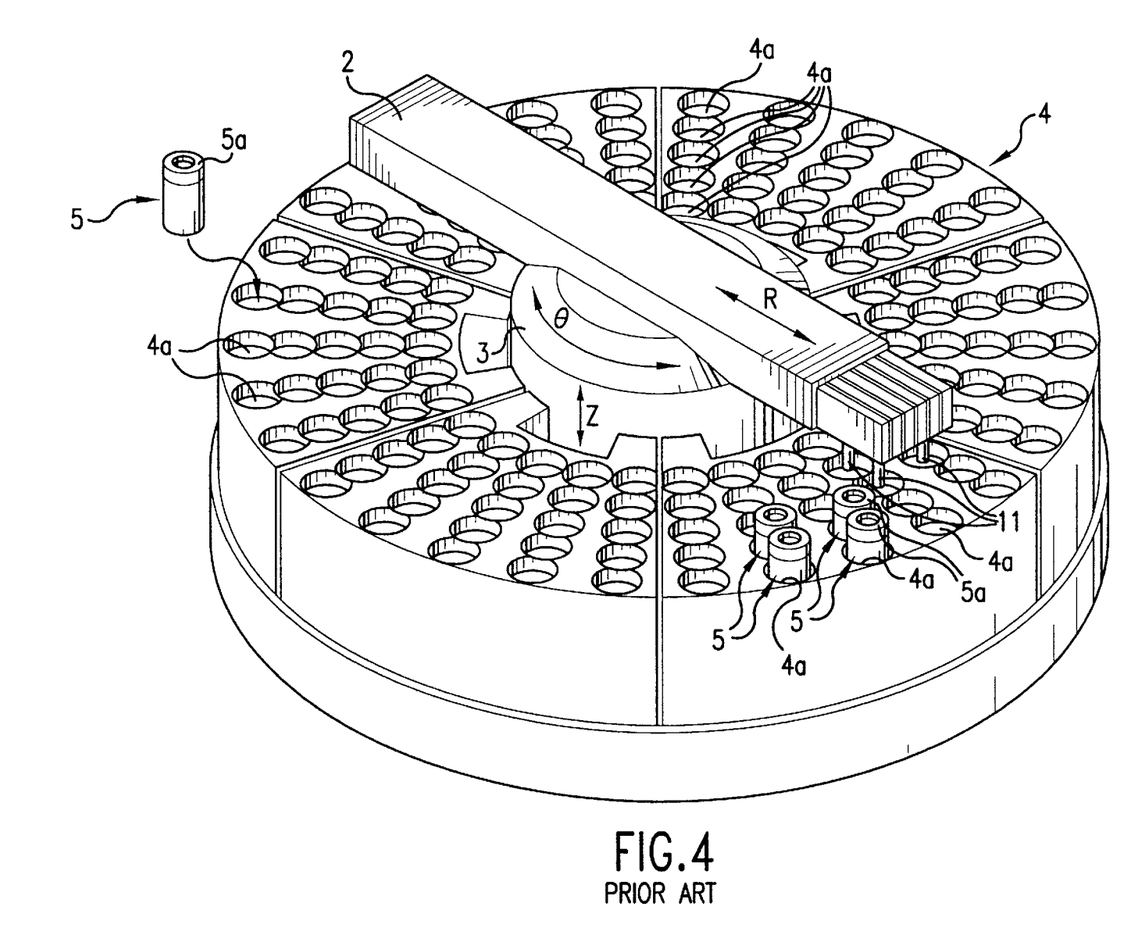
FIG. 4 is a perspective view showing a structure of a conventional automatic sampler.

An example of an automatic sampler which performs triaxial operations or movements in a cylindrical coordinate system is shown in FIG. 4. In the automatic sampler, around a cylindrical arm stand 3 for mounting an arm 2 at an upper end thereof, there is disposed a rack 4 in a disc shape, which is lower than the arm stand 3. The rack 4 is provided with a plurality of vial holes 4a on a ring-shaped upper surface thereof, and vials 5 can be inserted into the respective vial holes 4a. The vial 5 is a glass bottle containing a liquid sample, and on an upper end thereof, a cylindrical resin cap 5a is fitted. Incidentally, the cap 5a is provided to attach a rubber disc for closing an upper end opening of the vial 5, and in order to stick a needle to the rubber disc for sucking the liquid sample, a hole is formed in a center part of the cap. In the example of FIG. 4, in each of the rows arranged in the radial directions with an adequate angle on the upper surface of the rack 4, five vial holes 4a are formed at equal intervals. Also, an upper portion of the vial hole 4a is enlarged to have a tapered shape so that the vial 5 can be easily inserted therein.

The arm stand 3 rotates in a θ axis direction with respect to a lower stand, not shown, and at the same time, the arm stand 3 can move vertically or up and down in a Z axis direction. The arm 2 is provided with a gripper 1 (sample holding section) for holding the vial 5 at a longitudinal rod-shaped distal end. And, the arm 2 slides in the radial direction of the arm stand 3, i.e. it is movable in an R axis direction. Thus, by the arm 2 and the arm stand 3 (mechanism for moving the holding section), the gripper 1 can freely move (including rotational movement) above and around the rack 4 in the triaxial directions of the cylindrical coordinate system formed of the θ axis direction, the Z axis direction, and the R axis direction.

Figure 5:
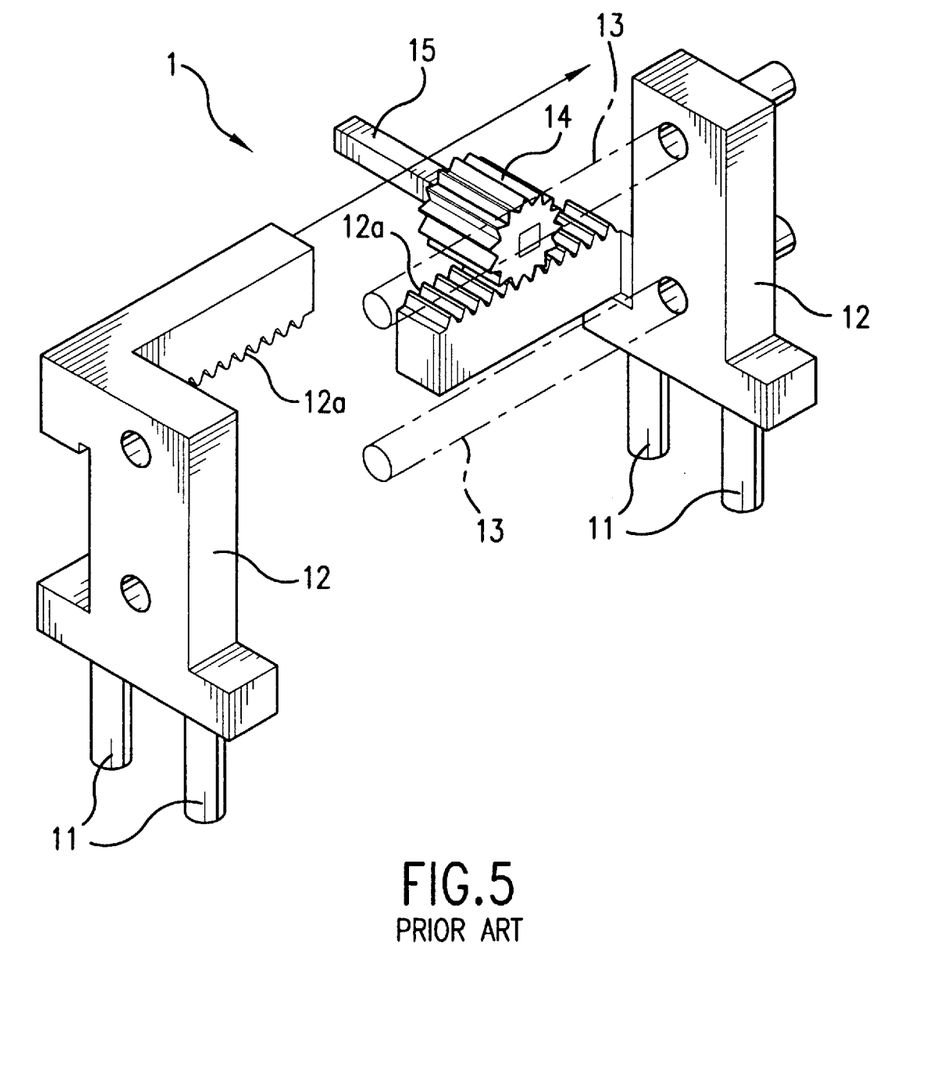
FIG. 5 is an exploded perspective view showing a structure of the conventional gripper.

The gripper 1 at the distal end of the arm 2 has four fingers 11 projecting downwardly, and by changing the width of a space or distance between these fingers 11 to be narrower or wider by a holding mechanism, the cap 5a of the vial 5 can be held or released. In the holding mechanism of the gripper 1, as shown in FIG. 5, two frames 12, each having two fingers 11 projecting downwardly, are fitted with two rods 13 so as to be slidable in the right and left directions. Also, in these two frames 12, racks 12a are disposed at upper and lower sides to project toward each other, and engage a pinion 14 disposed therebetween. The pinion 14 is a gear attached to a distal end of a square bar 15 which is freely rotatable and disposed in the longitudinal direction in the arm 2 shown in FIG. 4, and is driven from a side of the arm stand 3 through a bevel gear, not shown, fitted with the square bar 15. Thus, in the holding mechanism of the gripper 1, when the pinion 14 is rotated through the square bar 15 by driving force from the side of the arm stand 3, the space between the two frames 12 is expanded or reduced, so that the space between the two pairs of the fingers 11 extending from the two frames 12 can be expanded or narrowed.

Figure 6:
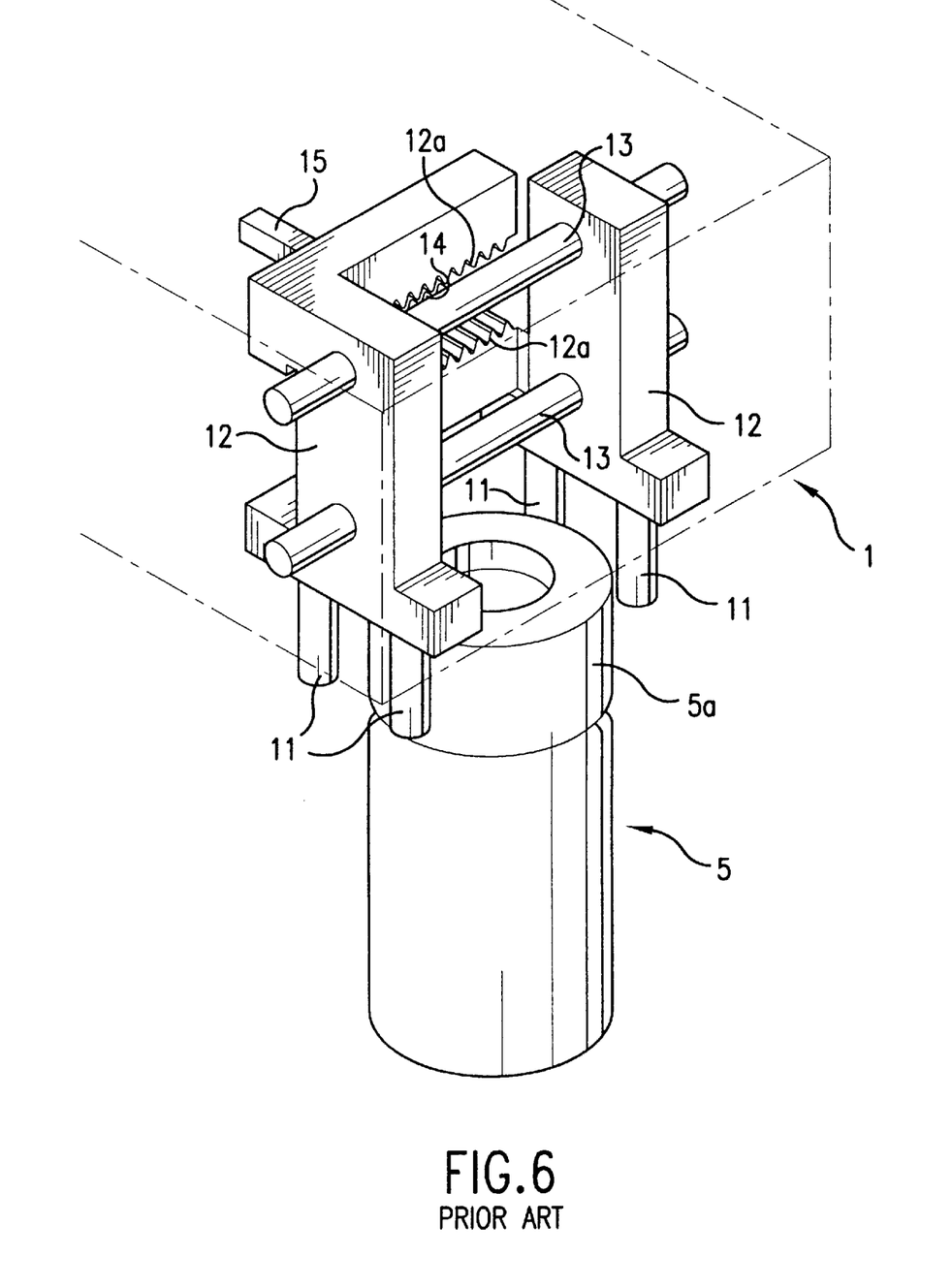
FIG. 6 is a perspective view showing the conventional gripper in which the fingers are opened.
Figure 7:
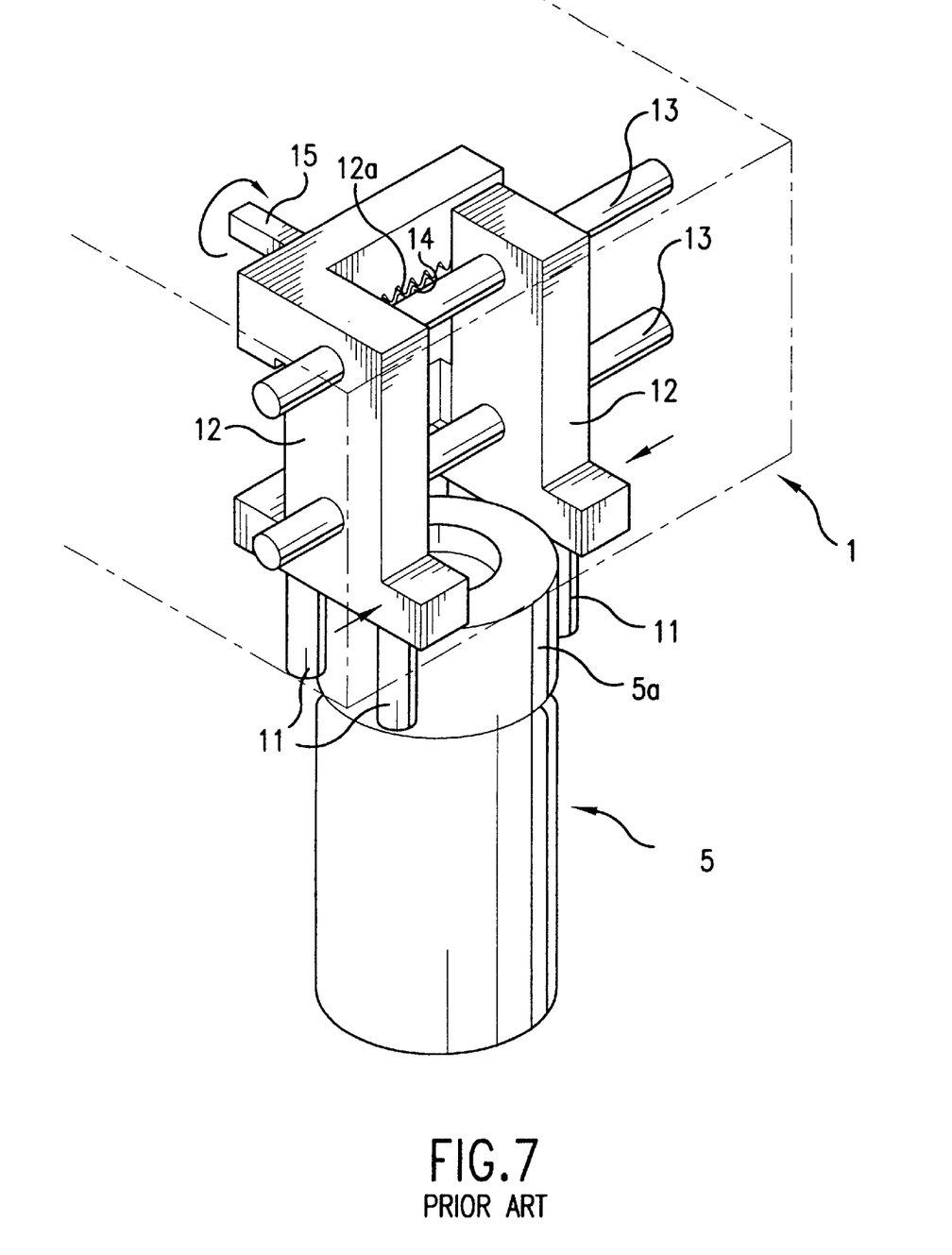
FIG. 7 is a perspective view showing the conventional gripper in which the fingers are closed.

In the automatic sampler as described above, the arm stand 3 is firstly elevated in the Z axis direction and then rotated in the θ axis direction, and at the same time, the arm 2 is moved in the R axis direction, so that the gripper 1 is located above the aimed or target vial 5. Then, after the space between the two pairs of the fingers 11 in the gripper 1 is expanded, the arm stand 3 is lowered in the Z axis direction to the holding position. Accordingly, as shown in FIG. 6, four fingers 11 with the expanded space therebetween are arranged so as to surround the cap 5a of the vial 5. Then, when the square bar 15 is rotated to close the space between the two frames 12 so that the space between the two pairs of fingers 11 is narrowed, as shown in FIG. 7, the cap 5a of the vial 5 is clamped and held among these four fingers 11. And, when the arm stand 3 is again elevated in the Z axis direction, the vial 5 in which the cap 5a is held by the fingers 11 of the gripper 1 is lifted up from the vial hole 4a in the rack 4. Further, by rotating the arm stand 3 in the θ axis direction and simultaneously moving the arm 2 in the R axis direction, the held vial 5 can be transferred to an analyzer or the like. Also, the vial 5, with which the process at the analyzer is finished, can be returned to the original vial hole 4a by reverse operations as described above.

As an alternate structure of the gripper 1 of the automatic sampler, there is a structure wherein a fork-shaped pawl is inserted from a side under the edge of the cap 5a to lift the cap 5a. If the above described gripper 1 is used, however, since it is required to have a wide space for sliding the pawl on the side of each vial 5, the vials 5 can not be closely disposed on the rack 4, so that a number of the vials 5 to be set would become extremely small. Also, instead of the gripper 1 using the aforementioned four fingers 11, there is a gripper using three fingers 11. In order to hold the periphery of the vial 5 from the three directions by using the gripper with three fingers 11, however, it is required to provide spaces for inserting the respective fingers 11 between the vials 5 in the three directions on the rack 4. On the other hand, if the vials 5 are arranged in a row normally, there are spaces for inserting the fingers 11 at four corners, so that in order to increase the number of the vials 5 which can be set on the rack 4 with the same area, using the four fingers as described above is advantageous.

In the aforementioned automatic sampler, the arm stand 3 is rotated in the θ axis direction and the arm 2 is moved in the R axis direction, so that the cap 5a of the aimed vial 5 is disposed in the center of the four fingers 11 of the gripper 1. However, since there is a mechanical error between the position of the gripper 1, which is located by moving the arm stand 3 in the θ axis direction and by moving the arm 2 in the R axis direction, and the actual position of the vial hole 4a on the rack 4, the cap 5a of the vial 5 is not always disposed at the center of the four fingers 11 of the gripper 1. Normally, however, as shown in FIG. 8, even if the cap 5a of the vial 5 is deviated from the center of the four fingers 11, as a distance between the two pairs of the fingers 11 decreases, the vial 5 is pushed by the finger 11 abutting or contacting the cap 5a at first (finger 11 located at upper right portion in FIG. 8) to move toward the central side of the four fingers 11, so that the accurate holding is possible.

Figure 9:
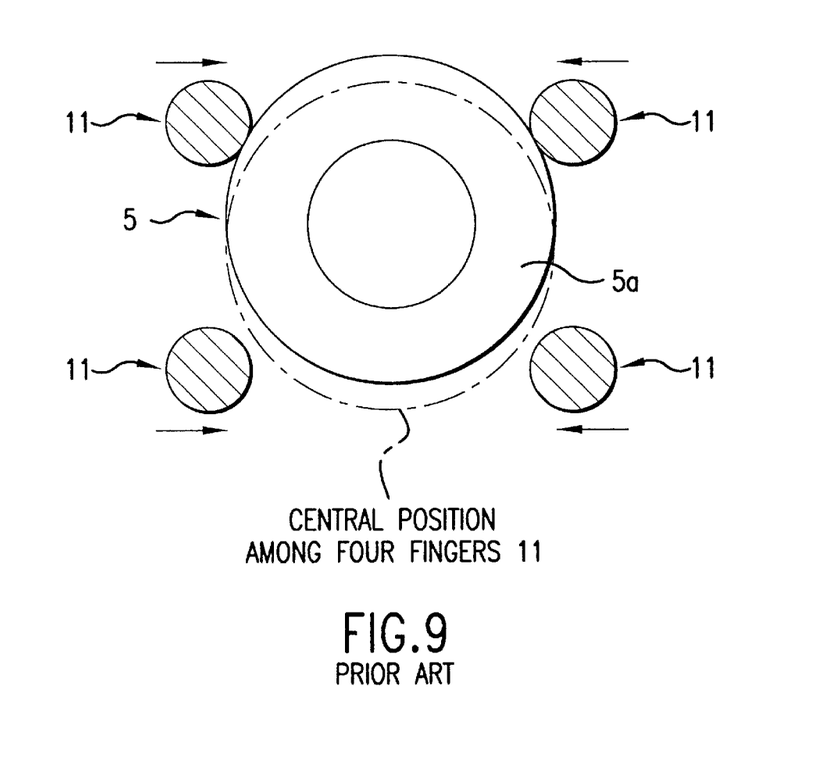
FIG. 9 is a plan view explaining an operation when the conventional gripper holds the vial insecurely.

As shown in FIG. 9, however, in case the position of the cap 5a of the vial 5 is deviated from the center of the four fingers 11, for example, toward the upper portion in the figure, the two fingers 11 in the upper side in the figure abut against the side surface of the cap 5a substantially at the same time from the right and left directions, so that there is a possibility that the cap 5a is clamped and held between these two fingers 11 without moving. Especially, in case silicone rubber or the like covers around the fingers 11 to increase frictional resistance for preventing the vial 5 from slipping off from the space between the fingers 11, even if the vial 5 is clamped between the two fingers 11, the vial 5 is not moved toward the central side smoothly. Thus, there is a high possibility that the vial 5 is caught between the fingers 11 and held therebetween incompletely. Namely, the reason why the vial 5 moves toward the central side is that when the fingers 11 push the cap 5a, sliding occurs between the fingers 11 and the cap 5a. Therefore, when silicone rubber or the like covers the periphery of the fingers 11, sliding of the cap 5a is deteriorated, and the cap 5a is held incompletely.

Figure 8:
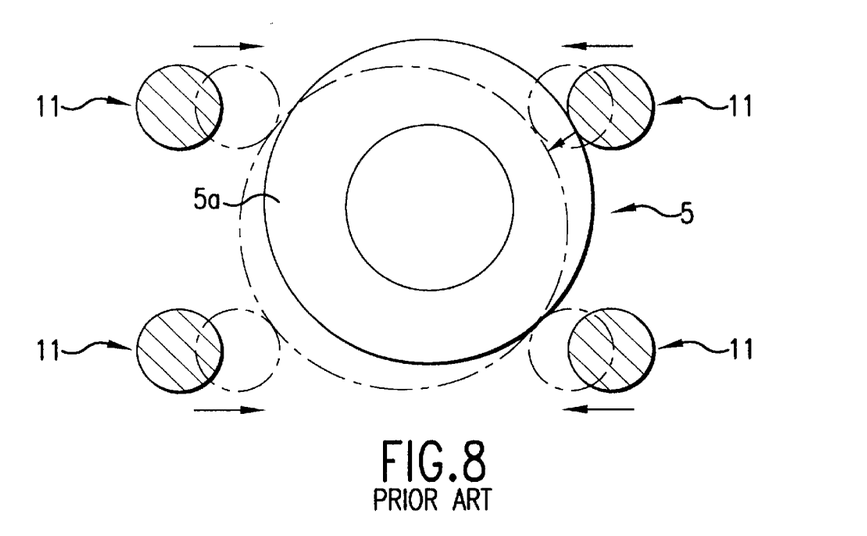
FIG. 8 is a plan view explaining an operation when a conventional gripper holds the vial normally.

Also, in the case shown in FIG. 8, when the vial 5 pushed by one finger 11 is not fully moved to the central side, as in the case of FIG. 9, the vial 5 is held by the two fingers 11. And, if the cap 5a of the vial 5 is held only by the two fingers 11 as described above, there is a possibility that when the vial is ascending in the Z axis direction, holding of the vial 5 is failed and the vial 5 can not be lifted up, or even if the vial 5 is held, when the vial is transferred or moved thereafter, holding of the vial 5 becomes unstable, so that the vial 5 is inclined or slipped on the halfway.

Therefore, in the conventional automatic sampler, when the gripper 1 holds the vial 5, if the vial 5 is not smoothly moved to the central side as a result of being pushed by the fingers 11, the vial 5 can not be securely held.

Incidentally, the aforementioned problem is not limited to the case of holding the vial 5 on the rack 4, but may occur similarly in the case of holding the vial 5 to return the vial 5 with which the steps or processes at the analyzer or the like are finished. Also, the gripper 1 is not limited to the case of using the four fingers 11, but also the same problem occurs as in the case of using three fingers 11 or five or more fingers 11.

Accordingly, the present invention has been made in view of the aforementioned problems, and an object of the invention is to provide an automatic sampler, which can always securely hold the sample.

Another object of the invention is to provide an automatic sampler as stated above, in which an elastic member is freely rotatably fitted onto the periphery of each finger of a sample holding section.

Further objects and advantages of the invention will be apparent from the following description of the invention.

SUMMARY OF THE INVENTION

To achieve the aforementioned object, the present invention provides an automatic sampler, wherein an elongated circular member or pipe is freely rotationally situated around each finger of a sample holding section, and when the fingers abut against a sample, the sample is pushed and smoothly transferred to a central side of the fingers while the elongated circular member is rotated, so that the sample can be securely held by all of the fingers. Also, in case the sample is held among three or more fingers accurately, since the sample is pushed by an elastic member on the outer peripheral surface of the elongated circular member, there is no possibility to slip off from a space among the fingers.

Incidentally, the sample is normally stored in a sample container such as a vial, and the sample holding section holds the sample together with the sample container.

DETAILED DESCRIPTION OF PREFERRED EMBODIMENTS

Hereinafter, embodiments of the present invention will be explained by referring to the attached drawings.

Figure 1:
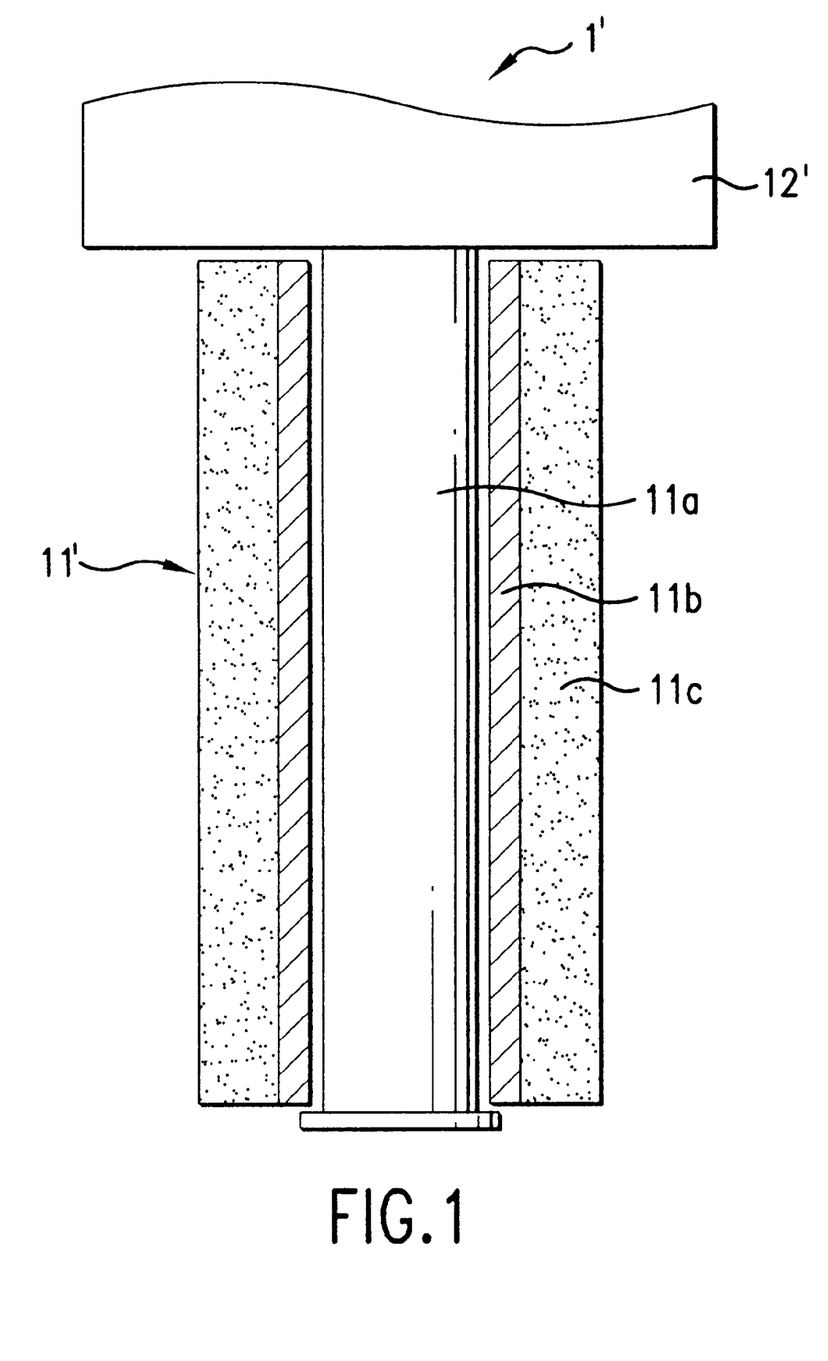
FIG. 1 is a partly cut sectional view showing a structure of a finger of a gripper according to an embodiment of the present invention.
Figure 2:
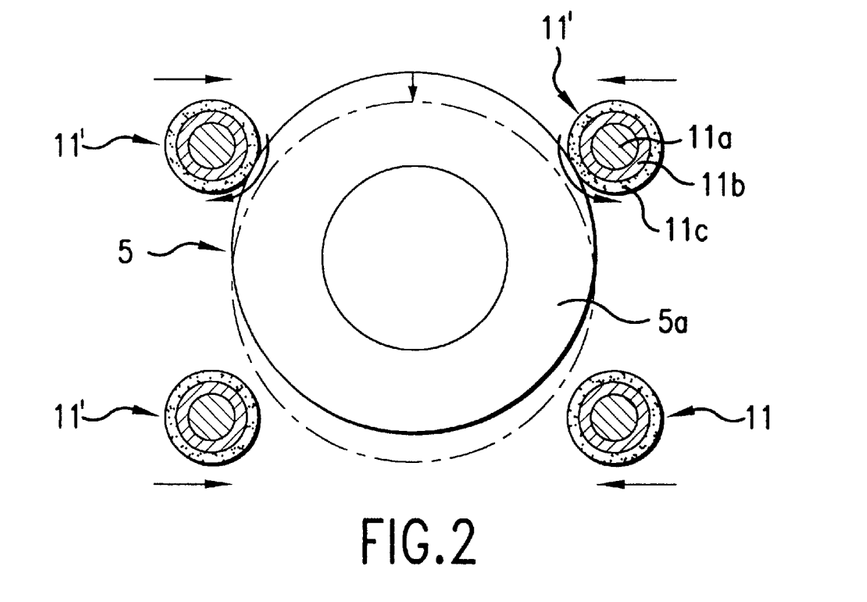
FIG. 2 is a plan view explaining an operation while the gripper is closing the fingers.
Figure 3:
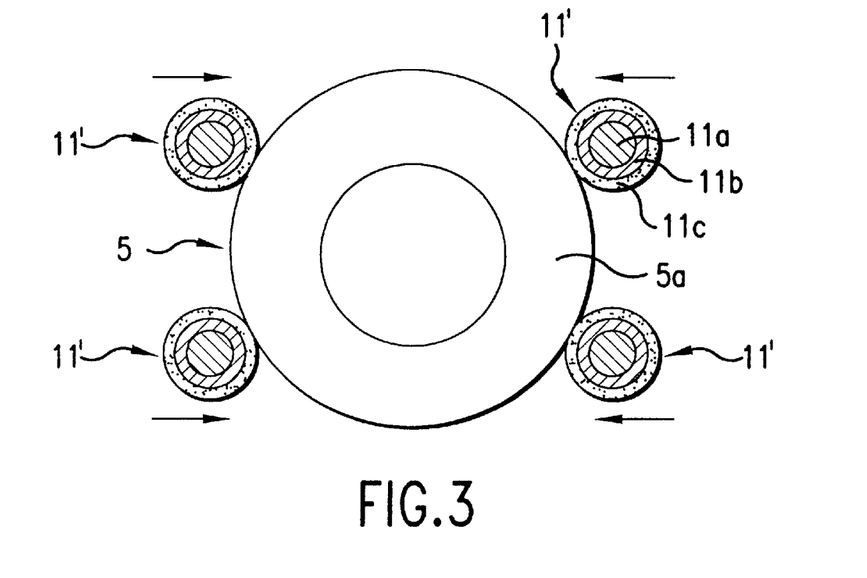
FIG. 3 is a plan view showing a state that the gripper finishes closing of the fingers.

FIGS. 1 through 3 show an embodiment of the present invention, wherein FIG. 1 is a partly cut sectional view showing a structure of a finger of a gripper; FIG. 2 is a plan view explaining an operation while the gripper is closing the fingers; and FIG. 3 is a plan view showing a state that the gripper finishes closing of the fingers. Incidentally, components or parts having the same functions as in the prior art shown in FIGS. 4 through 9 are designated by the same numerals.

In the embodiment of the present invention, there will be explained an automatic sampler for performing triaxial operations in a cylindrical coordinate system shown in FIG. 4. The present invention can be, however, practiced in automatic samplers performing other triaxial operations in a cylindrical coordinate system, or triaxial operations in an orthogonal coordinate system, or other operations.

In the automatic sampler in the embodiment, as explained in FIG. 4, the disc shape rack 4 is disposed around the periphery of the cylindrical arm stand 3 for mounting the arm 2, and the structures thereof are the same as in the prior art. Also, a distal end of the arm 2 is provided with a gripper 1' (sample holding section) structured substantially the same as in the gripper shown in FIGS. 5 through 7. Therefore, in the automatic sampler, the gripper 1' at the distal end of the arm 2 can freely move (including rotational motion) above and around the rack 4 in the triaxial directions of the cylindrical coordinate system formed of a θ axis direction, a R axis direction, and a Z axis direction. Therefore, the cap 5a of the vial 5 inserted in each vial hole 4a on the rack 4 is clamped by fingers 11', and transferred to the analyzer or the like, and the vial 5 that a processing was finished at the analyzer can be returned to the original vial hole 4a.

The fingers 11 of the conventional gripper 1 are mere plastic round rods, or the round rods covered with elastic members such as rubber. However, the finger 11' of the gripper 1' in the present embodiment is formed with a frame 12' as one unit, as shown in FIG. 1, and a base 11b is fitted with a clearance on an outer periphery of a plastic axis core 11a projecting downwardly from the frame 12'. By enlarging the lower end of the axis core 11a, the base 11b fitted therearound is prevented from falling off. The base 11b is a stainless steel pipe, and a silicone tube 11c is closely fitted on the outer periphery of the base 11b. The silicone tube 11c is a tube made of silicone rubber which is an elastic member. Accordingly, in this finger 11', the outer peripheral surface of the silicone tube 11c abuts against the side surface of the cap 5a of the vial 5. Also, the silicone tube 11c is, together with the base 11b, freely rotatable with respect to the axis core 11a.

When the gripper 1' having the fingers 11' as structured above holds the vial 5, since the side surfaces of the respective silicone tubes 11c of the four fingers 11' are pressed against the side surface of the vial 5 to closely contact and increase the frictional resistance thereto, while the vial 5 is being lifted or transferred, there is no possibility that the vial 5 is slipped off from the space among the four fingers 11'.

Also, as shown in FIG. 2, in case the position of the cap 5a of the vial 5 is deviated from the center of the four fingers 11' exactly upward in the figure, the silicone tubes 11c of the two fingers 11' in the upper side in the figure almost simultaneously abut against the side surface of the cap 5a from the right and left directions. Further, as the distance between the two fingers 11' is reduced, the silicone tubes 11c rotate together with the bases 11b, and move the vial 5 downwardly in the figure. Namely, in case the silicone tubes 11c do not rotate, the side surfaces of the silicone tubes 11c and the side surface of the cap 5a closely contact with each other without moving the vial 5, so that there might be a possibility that the cap 5a is clamped at the upper portion thereof in the figure. However, since the silicone tubes 11c rotate together with the bases 11b fitted with the clearance to the axis cores 11a, when the gripper 1' tries to reduce the space between the two fingers 11', turning effects or rotational forces always occur at the silicone tubes 11c, so that the cap 5a is surely pushed downwardly in the figure by this rotation. Therefore, even if the position of the vial 5 is deviated, since the deviated vial 5 is surely moved toward the central side of the fingers 11' by the fingers 11' which abut first, as shown in FIG. 3, it is possible to precisely clamp and securely hold the cap 5a of the vial 5 by the four fingers 11'. Further, as shown in FIG. 8, in case only one finger 11' abuts against the side surface of the cap 5a first, the gripper 1' operates in the same way.

As described above, according to the automatic sampler of the embodiment of the invention, even when the silicone tubes 11c are fitted around the outer peripheries of the fingers 11' to prevent the vial 5 from being slipped off, the deviated vial 5 can be surely moved toward the central side and held securely by the four fingers 11'. Thus, there is no possibility that the vial 5 is failed to be held and lifted up, or holding of the vial 5 becomes unstable so that the vial 5 is inclined or dropped off in the middle of transfer.

Figure 10A:
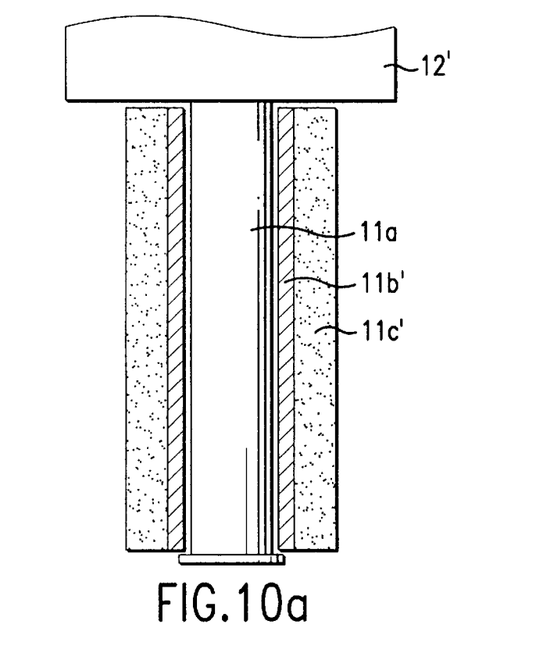
FIGS. 10(a) and 10(b) are partly cut sectional views for showing different examples of the fingers of the invention.
Figure 10B:
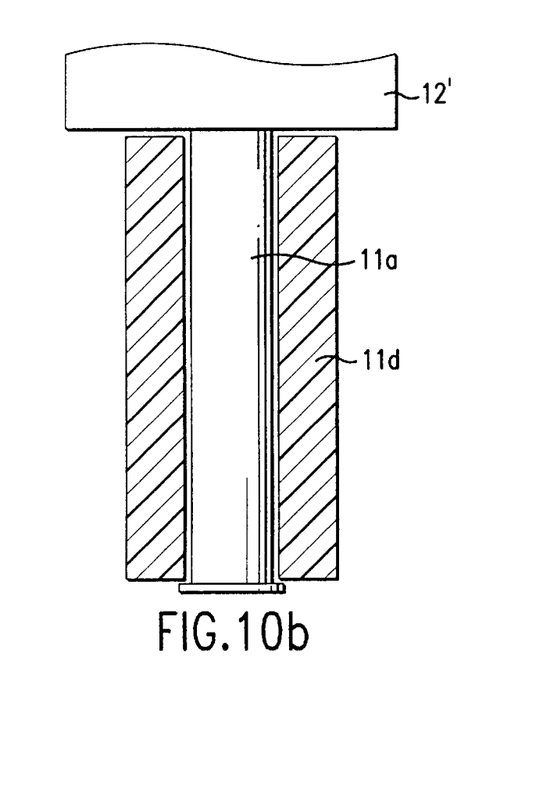

Incidentally, although in the finger 11' of the embodiment, the silicone tube 11c is fitted around the outer periphery of the base 11b, instead of the silicone tube 11c made of silicone rubber, there can be used a tube formed of elastic members made of other synthetic rubber or natural rubber, soft plastic or foamed soft plastic. Also, the elastic member 11c' may directly cover the outer peripheral surface of the base 11b' and integrally formed therewith (FIG. 10(a)), instead of forming as a tube. Further, as long as the base 11b is freely rotatably fitted around the axis core 11a, a material and a structure of the axis core 11a as a base part of the finger 11' are discretionary, and a material and a structure of the base 11b are also discretionary. Further, a pipe 11d formed exclusively of an elastic member may be freely and rotatably fitted around the axis core 11a directly (FIG. 10(b)). Namely, in the finger 11', the pipe having the elastic member at least around the outer periphery may be fitted freely and rotatably around the axis core.

Also, although the embodiment of the present invention shows the example in which the gripper 1 holds the cap 5a of the vial 5 by the four fingers 11', it is the same in case of using three fingers 11' or five or more fingers 11'. Further, a holding mechanism for actuating the fingers 11' is not limited to the one shown in the embodiment, and the fingers 11' divided into plural pairs may be moved by other mechanisms to narrow or expand the space therebetween. Also, each finger may be moved independently one by one to change the space between the fingers narrower or wider.

Also, in the embodiment of the present invention, the gripper 1' holds the sample stored in the vial 5, but in the present invention, it is possible to hold sample stored in a different container, or a cylindrical sample itself.

As being clear from the aforementioned explanations, according to the automatic sampler of the present invention, when one of the fingers in the sample holding section abuts against the sample, the sample is pushed while the elongated circular member or pipe is rotated, so that the sample can be moved smoothly toward the central side and securely held by all of the fingers. Therefore, it would not happen that the sample at the deviated position is held by parts of the fingers so that the holding of the sample is failed, the sample is held slantly, or the sample held once is dropped off on the way of being transferred. Consequently, errors in supplying the samples by the automatic sampler can be reduced, and process efficiency of the analyzer or the like can be improved.

While the invention has been explained with reference to the specific embodiments of the invention, the explanation is illustrative and the invention is limited only by the appended claims.

What is claimed is:

1. An automatic sampler for holding a sample, comprising:

a sample holding section having a holding mechanism, and at least three fingers projecting downwardly from the holding mechanism, said holding mechanism regulating a space defined among the fingers when it is actuated, each of said fingers having an elongated circular member with an elastic portion at least at an outer surface thereof and an axis fixed to the holding mechanism, said elongated circular member being rotatably attached around the axis to be freely rotatably attached to the holding mechanism so that when a sample is adapted to be held by the fingers, the fingers are properly located on the sample, and a moving mechanism attached to the holding section, said moving mechanism moving the sample holding section in plural directions.

2. An automatic sampler according to claim 1, wherein said elongated circular member includes a cylindrical base disposed over the axis, said elastic portion being fixed to the cylindrical base.

3. An automatic sampler according to claim 2, wherein said elastic portion is a cylindrical tube formed of a material selected from the group consisting of silicone rubber, natural rubber, synthetic rubber, a nonrigid plastic, and an elastic plastic foam.

4. An automatic sampler according to claim 2, wherein said elastic portion is directly coated onto the cylindrical base.

5. An automatic sampler according to claim 1, wherein said elongated circular member is formed of only the elastic portion rotatably situated around the axis.

6. An automatic sampler according to claim 1, wherein said sample holding section includes an arm, and an arm stand for mounting the arm, said holding mechanism being attached to a distal end of the arm and including at least two frames with racks, a pinion engaging the racks of the frames, and moving means for the pinion, said fingers being attached to the frames to extend downwardly therefrom so that when the moving means is actuated, the fingers attached to the frames move to change a distance between the fingers.

7. An automatic sampler for holding a sample, comprising:

a sample holding section having a holding mechanism, and at least three fingers projecting downwardly from the holding mechanism, said holding mechanism regulating a space defined among the fingers when it is actuated, each of said fingers having an elongated circular member with an elastic portion at least at an outer surface thereof and being attached to the holding mechanism to allow the elongated circular member to rotate freely relative to the holding mechanism so that in case an eccentric force is applied to the finger when a sample is adapted to be held by the fingers, the elongated circular member rotates to move the sample to a proper position for holding the sample correctly by the fingers, and a moving mechanism attached to the holding section, said moving mechanism moving the sample holding section in plural directions.

8. An automatic sampler according to claim 6, wherein each finger includes an axis attached to the holding mechanism, said elongated circular member being rotatable relative to the holding mechanism through the axis.

* * * * *